United States Patent [19]

Johnson

[11] 4,237,895
[45] Dec. 9, 1980

[54] CONTROL SIGNAL TRANSMITTER AND MONITOR FOR IMPLANTED PACER

[75] Inventor: Robert W. Johnson, Levittown, Pa.

[73] Assignee: Medcor, Inc., Hollywood, Fla.

[21] Appl. No.: 31,975

[22] Filed: Apr. 20, 1979

Related U.S. Application Data

[63] Continuation of Ser. No. 807,516, Jun. 17, 1977, abandoned.

[51] Int. Cl.³ .............................................. A61N 1/36
[52] U.S. Cl. ............................................. 128/419 PG
[58] Field of Search .................. 128/419 PG, 419 PT, 128/697

[56] References Cited

U.S. PATENT DOCUMENTS

| | | | |
|---|---|---|---|
| 3,171,892 | 3/1965 | Pantle et al. | 128/697 |
| 3,253,588 | 5/1966 | Vuilleumier | 128/903 |
| 3,618,615 | 11/1971 | Greatbatch | 128/419 PT |
| 3,631,860 | 1/1972 | Lopin | 128/419 PG |
| 3,651,799 | 3/1972 | Daynard | 128/419 PT |
| 3,662,759 | 5/1972 | Dabolt | 128/419 PG |
| 3,717,153 | 2/1973 | Bowers | 128/419 PG |
| 3,718,909 | 2/1973 | Greatbatch | 128/419 PT |
| 3,768,014 | 10/1973 | Smith et al. | 128/419 PT |
| 3,774,619 | 11/1973 | Goldberg | 128/419 PT |
| 3,805,796 | 4/1974 | Terry, Jr. et al. | 128/419 PG |
| 3,833,005 | 9/1974 | Wingrove | 128/419 PG |
| 3,945,387 | 3/1976 | Adams | 128/419 PG |
| 4,026,305 | 5/1977 | Brownlee et al. | 128/419 PG |
| 4,041,954 | 8/1977 | Ohara | 128/419 PT |
| 4,049,004 | 9/1977 | Walters | 128/419 PG |
| 4,124,031 | 11/1978 | Mensink et al. | 128/419 PT |
| 4,126,139 | 11/1978 | Walters et al. | 128/419 PG |

OTHER PUBLICATIONS

Thomas et al. "Medical & Biological Engineering", vol. 9, No. 5, Sep. 1971, pp. 503–509.

Primary Examiner—William E. Kamm
Attorney, Agent, or Firm—Dann, Dorfman, Herrell and Skillman

[57] ABSTRACT

A system for encoding and transmitting commands to effect modifications in the operating characteristics of an implanted pacer. A preferred embodiment of the system further comprises detection and display stages for use in monitoring pacer operation.

10 Claims, 4 Drawing Figures

CONTROL SIGNAL TRANSMITTER AND MONITOR FOR IMPLANTED PACER

This is a continuation of Ser. No. 807,516, filed June 17, 1977, now abandoned.

BACKGROUND OF THE INVENTION

This invention relates to the operation of implantable pacers, and more particularly to means for varying operating parameters of an implanted pacer and for monitoring pacer operation.

Various types of pacers are known for implantation in the body in order to control the operation of certain organs through the application of timed electrical pulses. The best known of these devices is the cardiac pacer which comprises a self-contained, battery powered pulse generator for applying timed, stimulating pulses to heart tissue of the wearer. Initially, pacers of this description operated at a fixed, invariant rate. Later the so-called "demand" type of pacer was developed and has generally superseded the fixed-rate pacer. With demand type pacers, pulses are produced only when a naturally-occuring heart-beat is not detected within some maximum time period. Various operating parameters of the pacer are of particular interest: the pulse width or duration; pulse amplitude; and sensitivity of the pacer to naturally-produced pulses are all of interest. It is a well known fact that some or all of these parameters, as well as the minimum pulse rate, should be tailored to suit an individual wearer. For this reason pacers are often constructed so that they may be adjusted before implantation to allow a physician to modify certain pacer characteristics as appropriate for a given wearer.

Although pacer adjustments are generally correct, in some cases it would be advantageous to be able to modify certain pacer operating characteristics after the pacer has been in use for some time. Accordingly, pacers have been designed which could be adjusted at will. In one approach, a pacer was provided with a movable magnetic element which could be manipulated by bringing another magnet close to the wearer's body, and manipulating the magnet adjacent the pacer. Still other approaches have been devised wherein sonic, ultrasonic, or radio frequency signals from an external signal generator are received by an implanted pacer, and the signals used to modify certain pacer operating characteristics. Examples of systems of this description are contained in U.S. Pat. No. 3,631,680; Lopin; U.S. Pat. No. 3,718,909; ; Greatbach; U.S. Pat. No. 3,805,796, Terry et al; U.S. Pat. No. 3,833,055; Wingrove; and U.S. Pat. No. 3,945,387; Adams. Most systems of the types disclosed in these patents comprise counters and decoders which count the number of signal pulses which are received and convert them into binary numbers which represent a desired mode of operation.

The application of a variable number of signal pulses is, for a number of reasons, not considered to be a totally satisfactory method of adjusting the parameters of an implanted pacer. Unless bulky, sophisticated checking systems are utilized there is no effective way for the pacer to recognize whether a proper number of pulses has been received. Proper adjustment of the pacer can only be verified by monitoring its operation; in other words, a trial and error procedure. If a spurious pulse, for instance one arising due to electromagnetic noise, occurs a significant change in the data will be effected. The same is true for the dropping of a pulse during the generation, transmission or detection of the data. For example, in one coding system 16 received bits would be decoded to produce the binary number 10000. Dropping a signal bit, so that only 15 pulses or accounts are received, would then produce the binary number 01111. Still further, according to prior art systems of the type illustrated above additional complete stages or data registers would be required for each additional process variable to be controlled.

It is also highly advantageous for a physician or technician to be able to easily monitor pacer operation. Ordinarily, monitoring of a pacer is accomplished by attaching electrodes to the body of the pacer wearer. Pacer pulses are then inferred from electrical signals picked up from the body tissue of the wearer. The pacer pulses, which thus must traverse substantial amounts of body tissue, may be substantially degraded; further, the signals may be difficult to accurately detect and interpret. It is apparent, moreover, that the physical connection of leads or sensors to an implanted pacer in order to obtain a direct reading is not practical. In addition, no means are presently known for eliciting a desired response from a pacer in order to check a mode of operation which the pacer does not ordinarily exhibit.

From the foregoing it should be understood that it would be desirable to provide means for easily varying the operating parameters of an implanted pacer at will; and moreover to monitor various pacer operating characteristics without the need for cumbersome and time-consuming electrode attachment procedures.

It is therefore an object of the present invention to provide a system for modifying the operating characteristics of an implanted pacer.

Another object of the invention is to provide improved means for monitoring the operation of an implanted pacer.

Still another object is to provide means for eliciting the specific responses from an implanted pacer, and monitoring the ensuing pacer operation.

SUMMARY OF THE INVENTION

Briefly stated, in accordance with one aspect of the invention the foregoing objects are achieved by providing an oscillator outputting a carrier signal, and means for modulating the carrier so that it exhibits a fixed number of signal pulses. In a preferred approach, the width of the pulses is modulated to exhibit a first, longer or a second, shorter duration. The signals are then applied to a transmitter stage which outputs them to an implanted pacer.

In a preferred embodiment a receiver is provided for detecting signals outputted by an implanted pacer, which represent pacer operating characteristics. When a pacer pulse is detected it is applied to the output signal encoder, enabling the latter so that a train of data pulses may be transmitted. The detected pacer pulses are also applied to first and second counter and display systems for displaying the interval between pulses and the width, or duration, of each succeeding pacer pulse.

In one embodiment a pulse comparator stage is also provided and serves to blank the pulse width display when pulse width exceeds some predetermined limit, signifying natural sinus rhythm operation.

BRIEF DESCRIPTION OF THE DRAWINGS

While the specification concludes with claims particularly pointing out and distinctly claiming the subject matter which is regarded as the invention, it is believed that the invention will be better understood from the following description of a preferred embodiment taken in conjunction with the accompanying drawings in which:

DESCRIPTION OF A PREFERRED EMBODIMENT

Figure 1:
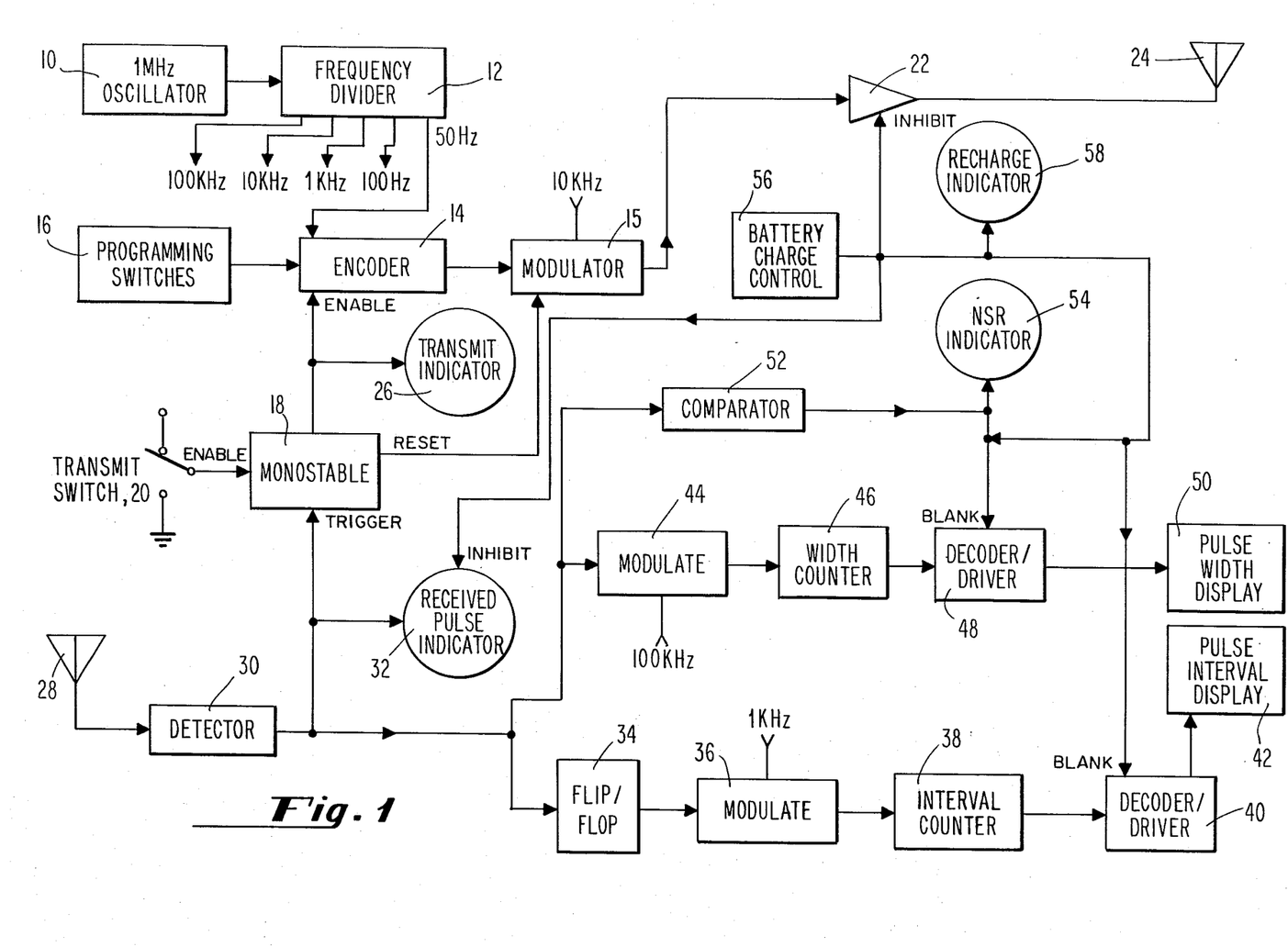
FIG. 1 is a functionalized diagram of a preferred embodiment of the system, including means for both controlling and monitoring an implanted pacer.

A master oscillator 10 operating at some fixed frequency, for instance, 1 MHz., feeds a frequency divider 12 having a plurality of outputs for supplying various points in the system with signals at appropriate frequencies. A 50 Hz. signal is supplied to an encoder 14. Operation of the encoder is controlled in part by a bank of programming switches 16. The encoder is enabled by means of a monostable circuit 18 which is in turn responsive to closure of a transmit switch 20, and to a trigger signal to be discussed hereinafter. The signals from encoder 14 are applied to modulator 15 which amplitude modulates a 10 KHz. carrier signal in accordance with the state of programming switches 16. Signals from modulator 15 are applied to an appropriate amplifier 22 and thence to an antenna 24 for transmission to an implanted pacer. Transmit indicator 26, which may for instance be an LED, serves to provide a visual indication of signal transmission.

In order to monitor the operation of an implanted pacer, a receiving antenna 28 is coupled to a detector 30. The received, detected signal is used to trigger monostable 18 and to enable another indicator 32 for denoting the reception of a pulse signal.

The detected signal is also applied to a flip-flop 34, the output of the flip-flop being modulated in modulator 36 with a 1 KHz. sine wave as shown. Interval counter 38 provides an indication of the interval between the modulated signals and serves to enable decoder/driver 40. The latter operates a display unit 42 for providing a visual indication of pulse interval time.

The detected, received signal is also applied to a modulator 44 along with a 100 KHz. signal. A pulse width counter 46 receives the modulated signal and applies it to a second decoder/driver 48, which in turn operates a second display 50. The latter provides an indication of the duration of pulses produced by the pacer being monitored.

Finally, the received signals, after detection, are applied to a pulse width comparator 52. An output from comparator 52 illuminates an NSR indicator and further serves to blank, or disable, display 50.

In a preferred embodiment of the present invention the system is self-contained, and powered by a battery. Accordingly, a battery charge control 56 is provided for monitoring the state of the battery (not shown) and for controlling current flowing thereto from a source of line current. A low battery condition is signaled by a visual recharge indicator display 58. The battery charge control is also coupled to the inhibit terminals of indicator 32 and decoder/driver stages 40, 48.

When the illustrated system is first energized oscillator 10 begins to operate, and frequency divider 12 outputs the indicated frequencies to appropriate points within the system. The application of the 50 Hz. signal to encoder 14 does not, however, enable the encoder and accordingly only a 10 KHz. carrier signal is transmitted after a suitable start-up delay to prevent accidental data transmission. The signal detection system is, however, immediately operable to detect and display indications of the operation of a pacer.

A pacer of the type intended for use with the present invention is disclosed in U.S. patent application Ser. No. 807,535 filed June 17, 1977. It is anticipated that the unit will be of the demand variety and probably (through not necessarily) be used for stimulating cardiac tissue of the wearer. The pacer is provided with a first, receiving antenna and appropriate detection and data processing circuitry for receiving, assimilating and storing especially coded signals. The pacer is further provided with a transmitting system responsive to received signals for outputting coded signals representing pacer operation, and more particularly the period and duration of pacer pulses. Accordingly, when a signal is received from transmitting antenna 24 the pacer responds by generating and transmitting a 5 MHz. signal modulated to reflect operation of the pacer. The 5 MHz. signal is received by antenna 28 and demodulated in detector 30.

In order to provide an operator of the inventive system with indications of pacer operation, the detected signal is applied to a flip-flop 34. The latter changes state with each received pulse, so that its output alternates in accordance with the period of succeeding pulses. The bistable output of flip-flop 34 is modulated by a 1 KHz. continuous wave carrier in modulator 36, and applied to an interval counter stage 38 which may, for example, be a decade counter. The latter outputs signals to decoder/driver stage 40 to cause the latter to enable a pulse interval display 42 in accordance with the received signal. Display 42 may be an LED four-digit display for indicating, in milliseconds, the interval between successive pulses.

The detected signal representing pacer operation is also applied to a modulator 44, wherein it is mixed with a 100 KHz. signal from frequency divider 12. The modulated signal is then applied to a width counter 46. The width counter serves to compute the time duration of each successive received pulse. This count is applied to decoder/driver stage 48 which outputs appropriate signals for energizing the pulse width display 50.

Like interval display 42, the pulse width display may comprise a four-digit LED display. Due to the considerably shorter time period to be monitored display 50 is advantageously provided with a decimal point in an appropriate position, and serves to read out the width of pacer pulses to one-hundredth of a millisecond.

Finally, the received and detected signal is applied to a pulse width comparator 52. The purpose of the latter is to distinguish between short artificial pulses (that is, tissue stimulating pulses produced by the pacer) and longer signal pulses produced by the pacer in response to a naturally-produced signal occuring at natural sinus rhythm (NSR). The width of longer pulses occurring at the NSR are of no value in quantitatively interpreting the operation of the pacer system, and accordingly the pulse width display 50 is rendered inoperative to avoid presenting possibly confusing information to the system operator. At the same time NSR indicator 54 is lit to inform an operator of the presence of natural sinus rhythm.

In order to modify the operating characteristics of the implanted pacer, as described in detail in the above-mentioned U.S. patent application Ser. No. 807,535, appropriately-coded pulses are generated at antenna 24 for application to the pacer. Preparatory to the transmission, various ones of programming switches 16 are set at appropriate positions. Switches may be provided for controlling pacer sensitivity, pulse width, pulse rate, or other variables. Further, in a preferred embodiment a switch is provided to modify the signal such that it can be loaded into a storage register, and thus "reprogram" the pacer.

In a preferred embodiment the status of various ones of the programming switches determine the nature of individual ones of a predetermined number of signal pulses. In the present embodiment, the pulse widths of a fixed number of N pulses is varied in accordance with the status of the switches. Accordingly, a data word having a fixed, invariant number of bits or signal pulses is always transmitted by the system; some characteristic of individual ones of the pulses, however, is varied to determine the content of the data word.

In order to effect transmission of a data word conforming with the status of the programming switches, transmit switch 20 is closed (in the present embodiment, coupled to ground). This enables, but does not actuate, monostable 18. The monostable circuit is constructed to operate for a time period in excess of any anticipated pacer pulse interval. A monostable period of, for example, 2.5 seconds may be selected.

When a pacer pulse arises and is detected by detector 30, the resulting signal is applied to monostable 18 at the trigger input thereof. The monostable immediately changes state, enabling encoder 14 and energizing transmit indicator lamp 26. The encoder proceeds to effect modulation of the 10 KHz. continuous wave signal in concert with modulator 15, as for example by interrupting the signal for a period corresponding to a long or short pulse width. In this manner the signals outputted by antenna 24 and received by the implanted pacer are caused to reflect the status of the various programming switches.

Although transmit switch 20 may be re-opened during the 2.5 second period of monostable circuit 18, the monostable will not then produce a reset signal. After the 2.5 second period terminates, however, the trailing edge of the monostable output signal is applied to modulator 15 and causes a final "resetting" signal pulse to be transmitted by output antenna 24. As more fully explained in copending application Ser. No. 807,535 the n+1th, or resetting, pulse serves to reset various elements of the data processing circuitry within the pacer, and provides a safeguard against pacer response to extraneous signals.

Figure 2A:
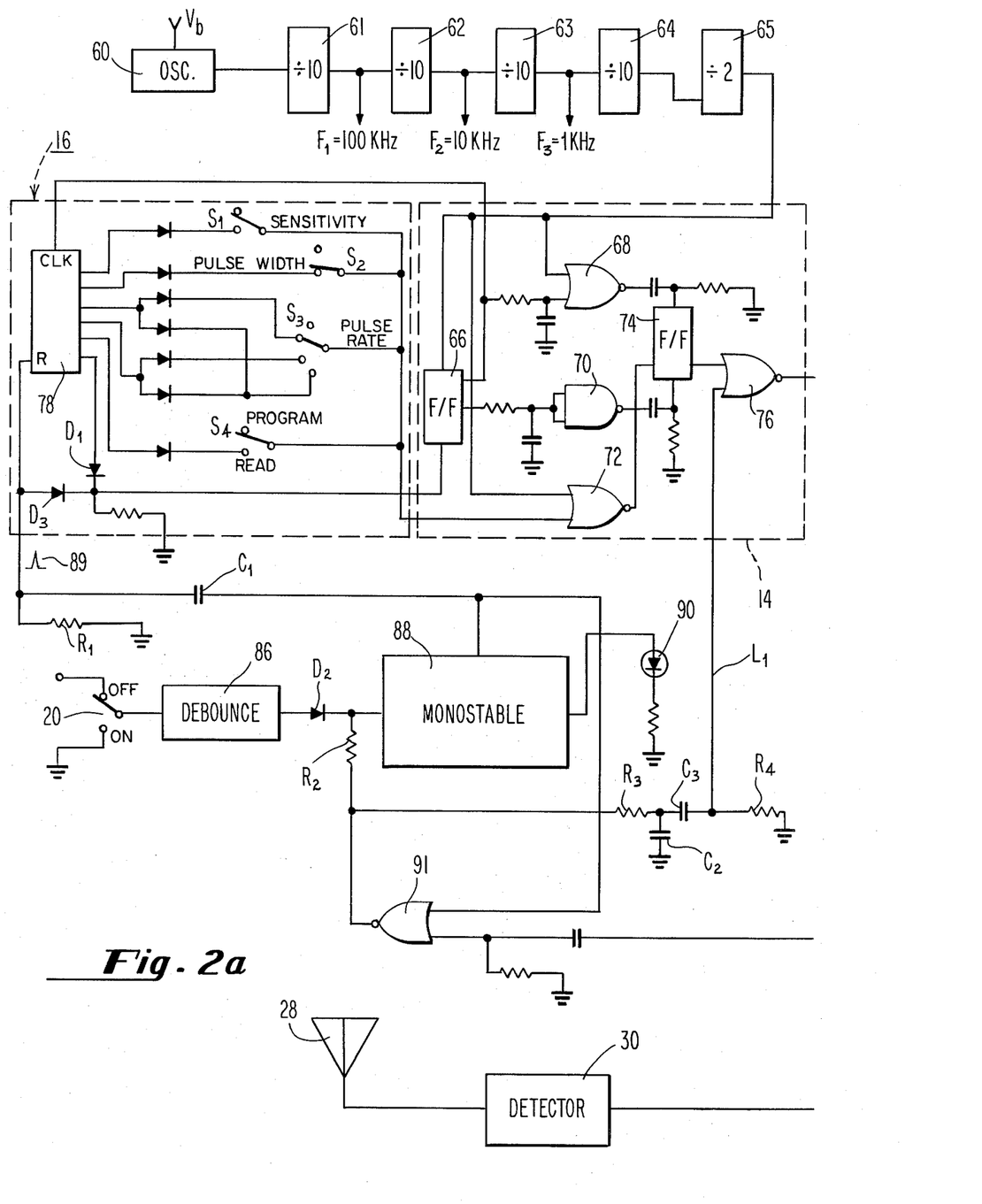
FIGS. 2a and 2b comprise a schematic diagram of a circuit for carrying out the functions of FIG. 1.
Figure 2B:
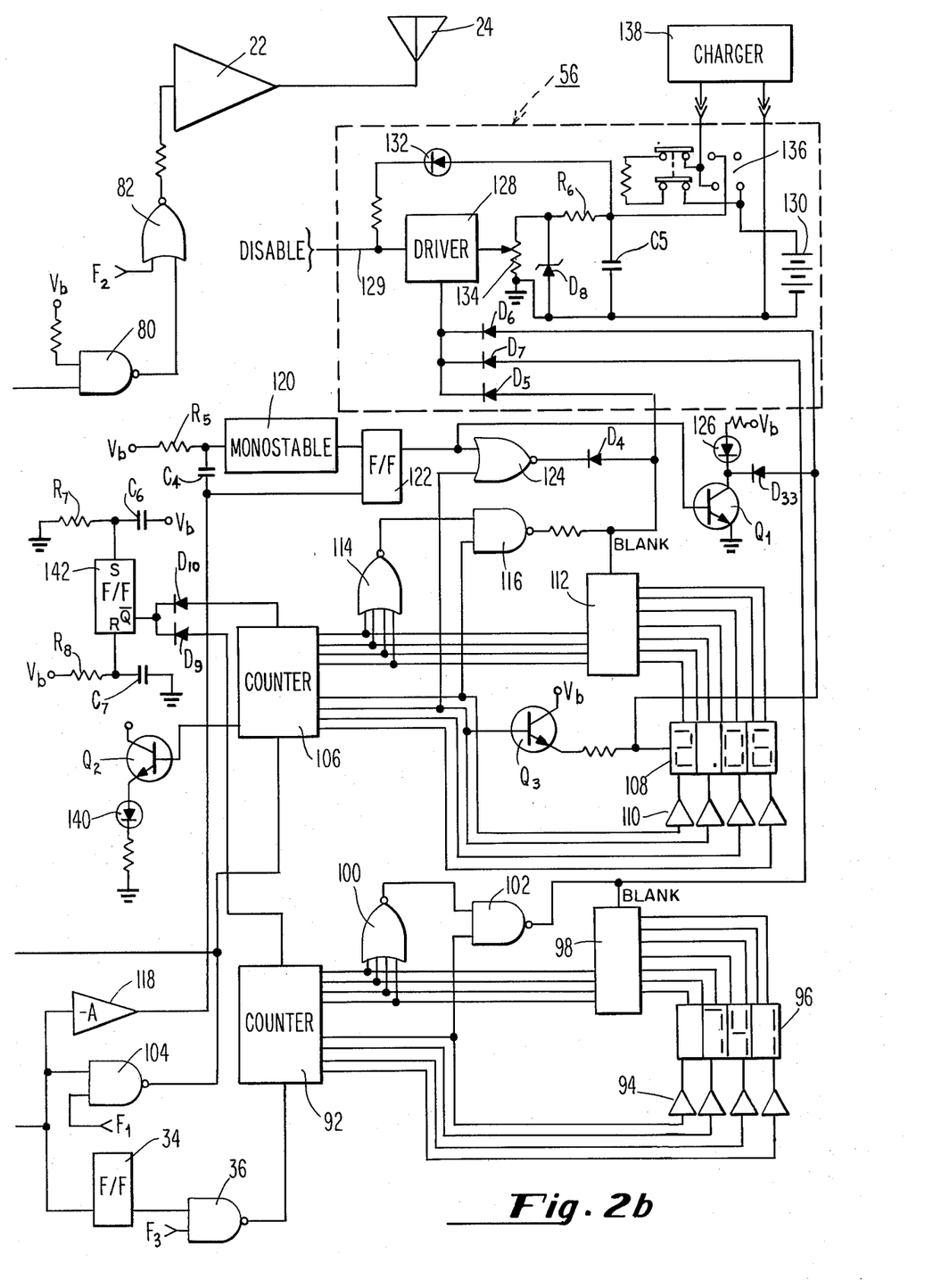

At FIG. 2 there is shown one specific execution of the embodiment disclosed in FIG. 1. A master oscillator 60, coupled to a source of appropriate potential $V_b$, produces a 1 MHz. output which is successively divided by factors of 10 by means of dividers 61–64. A final divider 65 divides by a factor of 2. Accordingly, frequency $F_1$ is 100 KHz., $F_2$ 10 KHz., $F_3$ 1 KHz. and the final output which is applied to encoder 14, 50 Hz. The encoder includes a flip-flop 66 which effectively serves as a divide-by-two frequency divider, and is coupled to NOR gate 68 and NAND gate 70. A second NOR gate receives the 50 Hz. input signal, as shown; and the two NOR gates, along with the NAND gate, are coupled to an output flip-flop 74. A final NOR gate 76 outputs a signal from the encoder unit.

The program switch module 16 comprises a shift register 78 having six coupled outputs, substantially as shown. Switching means $S_1$–$S_4$ are placed in series with each output for selectively coupling ones of the shift register outputs to the encoder. In the disclosed embodiment switches $S_1$–$S_3$ serve to control signals representative of pacer sensitivity, pulse width, and rate respectively. Switch $S_4$ controls the status of transmitted data, indicating whether or not the data is to be entered into the storage unit of a pacer. The final, lowermost output terminal of the shift register is coupled through a diode $D_1$ to flip-flop 66 for resetting the latter at the end of a transmitted word.

The signals outputted by encoded 14 are inverted by means of a NAND gate 80, and applied to NOR gate 82 along with a 10 KHz. frequency $F_2$. An output amplifier 22 receives the encoded, modulated signal and drives output antenna 24.

Transmit switch 20 selectively couples the input of a debouncing circuit 86 to battery potential $V_b$, or ground. Diode $D_2$ couples the debounce circuit to monostable 88, and an LED 90 provides an indication of the state of the monostable and accordingly the mode of operation of the latter unit. The monostable is coupled to reset terminal R of shift register 78 through a capacitor $C_1$ and resistor $R_1$, and to flip-flop 66 through a diode $D_3$. A NOR gate 91 provides feedback about the monostable through a resistor $R_2$. A low pass filter comprised of $R_3$, $C_2$ couples the output of NOR gate 91 to NOR gate 76; and a capacitor $C_3$ and resistor $R_4$ provide timing and DC isolation to NOR gate 76.

In order to receive signals transmitted by a pacer, input antenna 28 is coupled through a detector 30 of conventional design. The signals outputted by the detector are applied to a flip-flop 34 and thence to a modulator 36 which in a preferred embodiment comprises a NAND gate, as shown. The oscillations from flip-flop 34 are used to modulate the 1 KHz. frequency derived from frequency divider 63. The modulated signal is then coupled to a decade counter 92, the output of which operates a set of drivers 94 which are in turn coupled to a display 96. Other outputs from counter 92 drive decoder 98. NOR gate 100 and NAND gate 102 provide blanking of initial zeros, as will be discussed hereinafter.

The demodulated signals from detector 30 are also applied to a NAND gate 104 in concert with a frequency $F_1$ derived from frequency divider 61, and occurring at a rate of 100 KHz. The latter signal is coupled to a second counter 106, which provides signals to pulse width display 108 by way of a set of drivers 110. Other signals from decade counter 106 serve to operate a decoder 112 for energizing appropriate display elements. As was the case with the interval display circuit a NOR gate 114 is coupled to a NAND gate 116 to provide selecting blanking. An LED 140, driven by transistor $Q_2$ serves to provide a visual indication that counting is taking place.

A final output from detector 30 is applied to inverter 118 and thence to a monostable circuit 120 by way of a capacitor $C_4$. The upper plate of capacitor $C_4$ is normally biased through a resistor $R_5$. A flip-flop 122 coupled to the monostable, and to the lower plate of capacitor $C_4$, drives one input of NOR gate 124. The other input to gate 124 is derived from the second digit (constrained to be a decimal point) of the pulse width display unit 108. The output of flip-flop 122 also serves to drive a LED 126 through driver transistor $Q_1$ to provide an indication that received signals are occurring at natural sinus rhythm (NSR). The collector of drive transistor $Q_1$ is also coupled through an isolating diode $D_{33}$ to the decimal point terminal of pulse width display module 108. Blanking of pulse width display by disabling decoder 112 is effected by NOR gate 124 through diode $D_4$; and by a driver unit 128 of battery charge control 56 through diode $D_5$. Blanking of the decimal point of pulse width display 108, and blanking of interval display 96, is effected through diodes $D_6$ and $D_7$, respectively.

Driver 128 is responsive to the state of battery 130, and more specifically to the voltage thereof, for disabling portions of the illustrated system when battery potential falls to a predetermined minimum value. A "low battery" indication is provided by LED 132. The setting of driver 128 is accomplished by means of a potentiometer 134, coupled across a source of constant potential such as Zener diode $D_8$. The latter is connected in series with resistor $R_6$ and in parallel with a capacitor $C_5$. A charge control switch 136 is provided to allow manual control of battery charging. Finally, a battery charger 138, coupled to a source of outside current (not shown) may be included in the system.

In order to properly initialize the depicted system, the set terminal of a flip-flop 142 is coupled to a source of potential $V_b$ through a capacitor $C_6$, and to ground through resistor $R_7$. The reset terminal of the flip-flop is coupled to ground through a capacitor $C_7$, and to a point of bias potential $V_b$ through a resistor $R_8$. R-C circuits comprising $C_6$, $R_7$; and $C_7$, $R_8$ provide timing functions to allow the $\overline{Q}$ output of flip-flop 142 to initialize counters 92, 106 through diodes $D_9$ and $D_{10}$ respectively.

Figure 3:
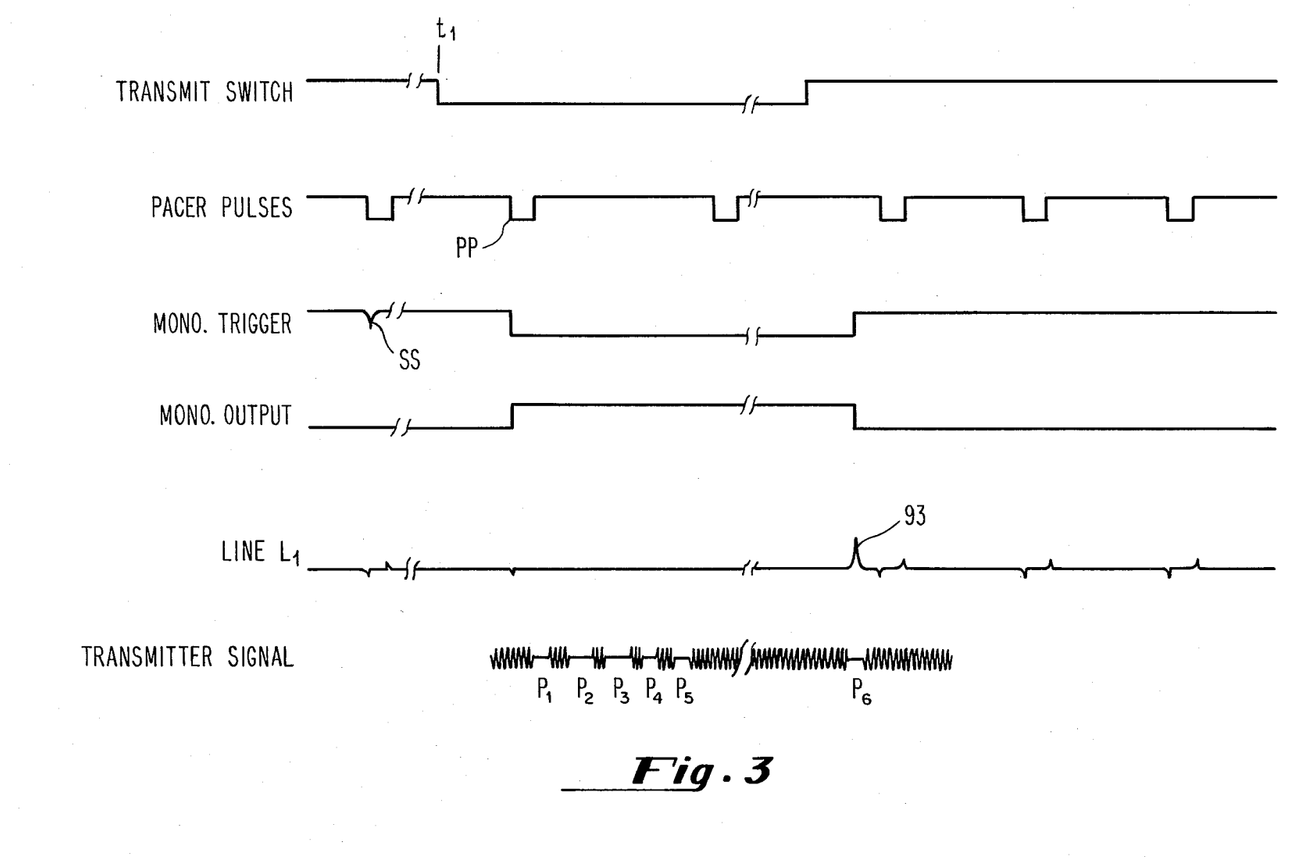
FIG. 3 is a timing diagram illustrating the operation of the system.

In connection with the following description of system operation, reference to the waveforms of FIG. 3 should be made for a full understanding of the activity within the system. When the system of FIG. 2 is first energized, oscillator 60 outputs a 1 MHz. signal which is successively divided by a factor of 10 by each of counters 61-64, and then by a factor of two by counter 65. A 10 KHz. signal is applied through OR gate 82 to output amplifier 22, driving antenna 24 so as to transmit a 10 KHz. unmodulated sine wave signal which is detected by appropriate circuitry within an implanted pacer. The latter operation is more specifically described in copending application Ser. No. 807,535, and for purposes of simplicity and brevity will not be repeated here.

In order to effect the modulation of the continuous wave 10 KHz. carrier, and thus transmit data to a pacer, transmit switch 20 is closed at time $t_1$. In the present embodiment closure of switch 20 is effected by moving it to its lower, or ground, contact. Irregularities or noise effected by switch operation are removed by debounce circuit 86 which may be a simple set of logic elements, as is familiar to those skilled in the art. By closing switch 20 the continuity with a source of bias potential $V_b$ is interrupted, so that diode $D_2$ is no longer forward biased. This action does not, however, trigger the monostable circuit 88 but rather prepared or enables the circuit to be triggered. Triggering of monostable 88 is effected by a negative-going pulse PP from NOR gate 91 so that monostable 88 may be characterized as being negative-edged triggered. As will be explained hereinafter, NOR gate 91 changes state in response to the detection of a pulse from the pacer being monitored. Accordingly, monostable 88 is triggered immediately subsequent to the occurrence of a pacer pulse.

Upon triggering a positive-going, square edged waveform is outputted by monostable 88. This signal is fed back through NOR gate 91 to overcome the enable signal at the monostable input, allowing the monostable to return to its quiescent state after some fixed period of time. This period, while not critical in length, should be greater than the longest anticipated interval between pacer pulses. Concurrent with its actuation, monostable 88 applies an appropriate voltage to LED 90, illuminating the latter and thus providing a visual indication of enablement of the data-producing portion of the system.

Consider now that transmit switch 20 is closed at time $t_1$, and that a pacer pulse PP has been detected by detector 30 and a triggering signal applied to monostable 88. If all of the various switches of shift register 78 are open a series of five pulses $P_1$–$P_5$ of 10 ms. duration and occurring at intervals of 40 ms. will be outputted from flip-flop 74 through NOR gate 76. The presence of these pulses at the lower input of NOR gate 82 will effectively clamp the latter, preventing it from gating in synchronism with the 10 KHz. frequency $F_2$ which is applied to the upper input of the NOR gate. Accordingly, for each of the five pulses a corresponding gap or cessation $P_1$–$P_5$ in the 10 KHz. signal outputted by NOR gate 82 will occur.

Amplifier 22 shapes and amplifies the signals outputted by NOR gate 82, driving output antenna 24 so that an RF carrier of 10 KHz., modulated by suitable interruptions, is provided. As further described in copending U.S. patent application Ser. No. 807,535 a receiver/decoder system in an implanted pacer senses the outputted signal, and responds thereto. The response may be to re-transmit signals denoting the operative state of the pacer and/or to reset or reprogram certain of the storage units which determine pacer operation. Accordingly, the width of each of the five transmitted pulses may be varied in order to transmit information in digital form.

To accomplish this, one or more of the switches coupling outputs of shift register 78 to NOR gate 72 are closed. As signals on various ones of the shift register outputs arise sequentially, the timing of the signals applied in the NOR gate 72 determines which of the five transmitted pulses are to be modified. For instance, should the pulse width switch $S_2$ be closed as shown in the Figure the second signal arising from shift register 78 is coupled to NOR gate 72, and serves to prolong the pulse outputted by flip-flop 74. In a preferred embodiment the initial pulse is lengthened from 10 to 30 ms. It will be understood, however, that the pulse interval remains constant at 40 ms.

In similar fashion other switches may be selectively closed so as to modify the duration (pulse width) of selected ones of the transmitted pulses. In this manner a form of pulse width modulation signaling is achieved; however, with the present system each given pulse denotes the intended status of a particular pacer operating parameter. Accordingly, the first-arising pulse in a train of data pulses, or word, applies to pacer sensitivity; the second pulse, to pacer pulse width; the third and fourth pulses, to pacer rate.

The fifth pulse $P_5$, constituting the final bit in the five-bit word to be transmitted according to this embodiment, constitutes a command indicating whether the data is to be loaded into the memory or storage element of the implanted pacer. In the present embodiment in order to allow loading of the data into the pacer memory a short pulse is required. Accordingly, in the "program" mode the fifth output of shift register 78 is decoupled from NOR gate 72. In the "read" mode (so called because only pacer monitoring is to be accomplished by the application of the data to the pacer) a "long" fifth pulse is provided. Appropriate decoding mechanism in the pacer system, as disclosed in the above-mentioned U.S. Patent application, respond to the length of the final pulse to enable or to prevent data loading, as appropriate.

The waveform of the output of monostable 88 traverses an RC circuit comprising $R_1$, $C_1$, as shown. Accordingly, a positive-going spike or pulse 89 is applied to reset terminal R of shift register 78. This serves to reset the shift register and enable the latter, so that the register will commence to produce outputs signals as soon as positive-going pulses are applied to its CLK terminal.

After some predetermined time monostable 88 times out and returns to its quiescent value. The output of NOR gate 91 again goes high, and the wavefront of the resulting square wave passes through RC circuits $R_3$, $C_2$; and $R_4$, $C_3$ to NOR gate 76. The initial RC circuit comprising resistor $R_3$ and capacitor $C_2$ is intended simply as a low-pass filter which prevents spurious signals (SS, FIG. 3), which may be effected by detected pacer pulses at time when monostable 88 is not actuated, from continually interrupting the 10 KHz. carrier. When NOR gate 91 changes state, however, its positive-going and persisting output pulse traverses capacitor $C_3$ and the resulting positive pulse (93, FIG. 2) is applied to the lower input of NOR gate 76. The resulting signal is passed through invertor 80 and applied to OR gate 82. The signal then modulates the continuous wave 10 KHz. carrier to cause a final bit $P_6$ to be transmitted by antenna 24.

It will now be appreciated that if transmit switch 20 is held in the "ON" position longer than it take monostable 88 to time out, the bias at the upper input of NOR gate 91 will traverse resistor $R_2$ and will prevent pulse 93 from occurring until transmit switch 20 is released. In either event, that is, either after some predetermined period of time or when the transmit switch is purposely released, pulse 93 is transmitted. Due to the relatively brief time required for the encoding and transmission of a data word, pulse 93 will almost invariably arise after the end of such word. The final or sixth bit serves to reset the data processing circuitry within the pacer. This feature adds to the data response integrity of the pacer, and comprises the first stage in preparing the pacer for the receipt of a new data word, if desired.

As indicated above, and more fully described in co-pending patent application Ser. No. 807,535 the implanted pacer which is to be monitored and/or reprogrammed by the illustrated system is adapted to produce a modulated RF signal which may be detected in order to monitor pacer operation.

The signals outputted by the pacer are received by antenna 28 and demodulated by means of a detector 30 of conventional design. The detected signal is then applied to sensing and display circuitry which serves to inform an operator of the mode of operation of the pacer, and to quantitatively inform him of certain pacer operating characteristics.

It is extremely desirable to be able to monitor the interval of pulses being produced by a pacer. As known by those skilled in the art, the interval of pacer pulses comprises a measure of the status of the pacer battery, and accordingly pacer pulse interval is a significant parameter in terms of evaluating the remaining life of a pacer battery.

Accordingly, the detected signals are applied to a flip-flop 34. The flip-flop output is applied to NAND gate 36 along with a 1 KHz. signal, and so modulates the latter. The resulting, modulated 1 KHz. signal is coupled to the CLK input of decade counter 92. The latter then produces successive outputs which simultaneously enable each of four 7-bar display units of an interval display 96 by way of drivers 94. One display module which operated satisfactorily in a test system was a Hewlitt-Packard 5082/7404 four digit display.

Signals for effecting energization of appropriate 7-bar display elements are also produced by decade counter 92, and applied to decoder 98. The decoder, which may for example be a model CD4511BE manufactured by RCA, produces a signal on selected ones of its seven output terminals for energizing appropriate display elements. In this manner, counter 92 effectively selects a specific display member to be driven, and the elements of the 7-bar display to be eliminated. By scanning the intervals display at an appropriately rapid rate all elements remain effectively illuminated.

In order to enhance the readability of the display the present invention includes means for blanking zeros when they appear as the most significant digit in the display. Accordingly, rather than displaying a "0741" the illustrated unit displays only "741". Leading zero blanking is effected by NOR gate 100, which is coupled to all four upper outputs of decade counter 92, and to a NAND gate 102 whose other input is derived from the signal used to energize the driver of the first display window.

In order to determine the width of pulses being produced by the pacer, the detected pacer pulse signal is applied to a NAND gate 104 along with a 100 KHz. signal. The pulse modulates the 100 KHz. signal and the thus-modulated signal is applied to a second decade counter 106. The latter in effect counts the received pulses and outputs signals represented thereof. A first signal which represents the significance or place of a numeral is applied to appropriate portions of display 108 through drivers 110. Other signals, which represent the value of individual numerals, are applied to decoder 112. As is familiar to those skilled in the art, the latter energizes appropriate members of the seven bars of each display in order to cause a given numeral to be found. Decoder 112, like the corresponding unit used for interval display, may be a commercially available CD4511BE unit available from RCA. Similarly, in a preferred embodiment the pulse width display comprised a Hewlitt-Packard 5082-7404 four-digit display unit.

In the disclosed embodiment pulse interval information is resolved to one millisecond, while pulse width signals are resolved to 0.01 ms. Accordingly, it is necessary to display a decimal point in the second digit's place of display unit 108. To effect this a driver transistor $Q_3$ is coupled to an appropriate input terminal of the four-digit display, as shown. This maintains the second digit's place blank, except for the decimal point. Also as described with respect to the interval display, a leading-edge zero inhibit circuit including NOR gate 114 and NAND gate 116 is provided to insure that the leftwardmost digit of any given display will never be zero.

Finally, the output of detector 30 is applied through an inverter 118 to monostable 120 by means of capacitor $C_4$. The RC circuit including $R_5$ and $C_4$ allows only leading and trailing edges of the demodulated signal to be applied to the monostable. The leading edge of the negative-going demodulated signal triggers the monostable, causing it to begin timing, while the trailing edge of the signal trips flip-flop 122. If the monostable times out after the end of the demodulated pulse, the pulse is considered to be a relatively short or "narrow" pulse and flip-flop 122 outputs a digital zero to NOR gate 124. A relatively long (greater than 2 ms.) pacer pulse will cause flip-flop 122 to output a digit 1 to NOR gate 124, and to driver transistor $Q_1$ for energizing an NSR indicator LED 126.

Here it should be noted that it is wished to monitor pulse characteristics only when a patient's heart is not operating in NSR. Accordingly, a narrow pulse, i.e., one of substantially less than 2 ms. duration, indicates pacer operation inasmuch as the detected pacer-generated pulses are substantially narrower than NSR pulses. The present system then indicates NSR operation by causing NOR gate 124 to output a digital 0, inhibiting decoder 112 to blank display 108, and further by illuminating LED 126 to immediately signify an NSR operation.

In a preferred embodiment the present invention comprises a hand-held battery operated module which may be conveniently manipulated by a user so as to place it directly against the chest of a patient whose pacer is to be monitored. A battery 130 is disposed in a common housing with the illustrated circuitry, and its status monitored by a circuit which is sensitive to a drop in battery voltage which signifies a need for replacement or recharging of the battery. Accordingly, with switch 136 in its central position battery 130 is placed across filter capacitor $C_5$, and across the series combination of $R_6$ and Zener diode $D_8$. A voltage taken from the slider of potentiometer 134 then provides a source of fixed, reference voltage for operating a comparator 128. At the same time part of the actual battery potential is applied to the comparator. When actual battery potential drops below a predetermined point output line 129 of comparator-driver 128 goes low, energizing warning LED 132 and disabling the 10 KHz. oscillation, transmission and detection stages of the circuit. The lowermost line of comparator 128 is driven to a digital 0 potential to disable counters 98 and 112 through diodes $D_7$ and $D_5$ respectively. Operation of received pulse indicator LED 140 is prevented by disabling driver transistor $Q_2$. Further, the decimal point display of the pulse width display unit 108 is blanked through diode $D_6$. In this manner no programming or monitoring will take place until battery 130 is replaced or recharged.

To facilitate recharging of the battery a charger stage 138, which may be of any appropriate type, is coupled to battery 130 through switch 136 so that recharging of the battery may proceed.

It will now be seen that there has been disclosed herein an apparatus for not only monitoring the operation of an implanted pacer, but for adjusting it and resetting pacer parameters to modify pacer operation at will. It should be evident from the foregoing description that certain aspects of the invention are not limited to the particular details of the examples illustrated, and it is therefore contemplated that other modifications or applications will occur to those skilled in the art. It is accordingly intended that the appended claims shall cover all such modifications and applications as do not depart from the true spirit and scope of the invention.

What is claimed as new and desired to be secured by Letters Patent of the United States is:

1. Control means for modifying the operation of an implanted pacer by a programming signal, comprising:
    oscillator means for producing a carrier signal;
    encoder means for modulating said carrier signal to provide the programming signal having an invariant number of data bits;
    programming means coupled to said encoder means for selectively varying a characteristic of predetermined ones of said data bits; and
    an output transmitter coupled to said encoder means for directing a programming signal to the implanted pacer.

2. Control means according to claim 1, further including receiver means for detecting the occurence of a signal transmitted by an implanted pacer representing a pacer pulse; and
    means connected to said receiver means for allowing the modulation of said carrier signal upon the detection of said pacer pulse.

3. Control means according to claim 2, wherein the output transmitter signal is an electromagnetic radio frequency signal.

4. Control means for modifying and monitoring the operation of an implanted pacer, comprising:
    means for generating a programing signal having a train of an invarient number of data pulses, each of said data pulses exhibiting either a first or a second state;
    programming means for controllably varying the state of individual ones of said data pulses;
    transmitter means for receiving and amplifying said train of data pulses and directing them to an implanted pacer;
    receiver means for detecting a signal transmitted by an implanted pacer representative of a pacer pulse and for generating a pacer pulse signal in response thereto;
    driving means coupled to said receiver means and responsive to said pacer pulse signal for producing an output signal representing a characteristic of pacer pulses; and
    display means coupled to said driving means and responsive to said output signal for displaying information representing said pacer pulse characteristic.

5. Control means according to claim 4, wherein said driving means comprises counter means and decoder means.

6. Control means for modifying and monitoring the operation of an implanted pacer, comprising:
    means for generating a programming signal having a train of an invariant number of data pulses, each of said data pulses exhibiting either a first or a second state;
    means for controllably varying the state of individual ones of the data pulses in accordance with a desired mode of pacer operation;
    transmitter means for amplifying said train of data pulses and for directing them to an implanted pacer;
    receiver means for detecting a signal transmitted by the implanted pacer representative of a pacer pulse and for generating a pacer pulse signal in response thereto;
    first counter means coupled to said receiver means and responsive to said pacer pulse signal for producing a first signal representing the interval between pacer pulses;

first decoder means coupled to said first counter means for producing a first display signal;

first display means coupled to said first decoder means for displaying information representing said interval;

second counter means coupled to said receiver means and responsive to said pacer pulse signal for producing a second signal representing the duration of a pacer pulse;

second decoder means coupled to said second counter means for producing a second display signal; and second display means coupled to said second decoder means for displaying information representing said duration.

7. Control means according to claim 6, further including gating means coupled to said receiver means and to said data pulse train generating means for enabling said data pulse train to be generated subsequent to the occurrence of a pacer pulse.

8. Control means according to claim 7, further including timer means coupled to said encoder means for producing a resetting signal at least a predetermined period of time after the occurrence of the last one of said data pulses.

9. Control means according to claim 8, wherein said predetermined period of time is not less than the maximum interval between pacer pulses.

10. Control means according to claim 9, wherein the generated train of data pulses comprises interruptions of a carrier signal, said first or second state of said data pulses being manifested by the duration of the individual interruptions.

* * * * *

UNITED STATES PATENT AND TRADEMARK OFFICE
CERTIFICATE OF CORRECTION

PATENT NO. : 4,237,895
DATED : December 9, 1980
INVENTOR(S) : Robert W. Johnson

It is certified that error appears in the above—identified patent and that said Letters Patent is hereby corrected as shown below:

Column 1, line 51, delete superfluous semicolon (;).
Column 4, lines 15-16, "especially" should read --specially--
         line 58, "occuring" should read --occurring--
Column 7, line 3, "$D_{33}$" should read --$D_3$--
Column 9, line 10, "waveform" should read --wavefront--
         line 13, delete "of" after "R"
Column 12, line 16, "occurence" should read --occurrence--

Signed and Sealed this

Ninth Day of June 1981

[SEAL]

Attest:

RENE D. TEGTMEYER

Attesting Officer     Acting Commissioner of Patents and Trademarks